US009921226B2

United States Patent
Faegh et al.

(10) Patent No.: US 9,921,226 B2
(45) Date of Patent: Mar. 20, 2018

(54) SENSOR SYSTEM UTILIZING PIEZOELECTRIC MICROCANTILEVER COUPLED WITH RESONATING CIRCUIT

(71) Applicant: Northeastern University, Boston, MA (US)

(72) Inventors: Samira Faegh, Boston, MA (US); Nader Jalili, Newton, MA (US); Srinivas Sridhar, Newton, MA (US)

(*) Notice: Subject to any disclaimer, the term of this patent is extended or adjusted under 35 U.S.C. 154(b) by 333 days.

(21) Appl. No.: 14/778,779

(22) PCT Filed: Apr. 8, 2014

(86) PCT No.: PCT/US2014/033287
§ 371 (c)(1),
(2) Date: Sep. 21, 2015

(87) PCT Pub. No.: WO2014/168924
PCT Pub. Date: Oct. 16, 2014

(65) Prior Publication Data
US 2016/0054329 A1 Feb. 25, 2016

Related U.S. Application Data

(60) Provisional application No. 61/809,734, filed on Apr. 8, 2013.

(51) Int. Cl.
*G01N 29/036* (2006.01)
*G01N 29/02* (2006.01)
(Continued)

(52) U.S. Cl.
CPC .............. *G01N 33/66* (2013.01); *G01G 3/16* (2013.01); *G01N 29/022* (2013.01);
(Continued)

(58) Field of Classification Search
CPC ............. G01N 29/022; G01N 33/5438; G01N 29/036; G01N 33/66; G01N 2291/0257; G01G 3/16
(Continued)

(56) References Cited

U.S. PATENT DOCUMENTS 5,719,324 A * 2/1998 Thundat ............... G01N 29/022
422/88
8,524,501 B2 * 9/2013 Adams ................. G01N 29/022
422/88
(Continued)

OTHER PUBLICATIONS

Faegh, et al., "A Cost-Effective Self-Sensing BioSensor for Detection of Biological Species at Ultralow Concentrations," J. Appl. Phys., vol. 113, 224905-1-224905-8 (2013).
(Continued)

*Primary Examiner* — J M Saint Surin
(74) *Attorney, Agent, or Firm* — Posternak Blankstein & Lund LLP

(57) ABSTRACT

An interchangeable sensor system is described, including: a microcantilever including a beam anchored at a first end, the beam being free to vibrate on another end, wherein a piezoelectric layer is deposited on a surface of the beam; an input configured to receive a voltage from a voltage source for applying voltage to the piezoelectric layer; and a resonating circuit including: the piezoelectric layer, configured as a capacitor of the resonant circuit; and one or more additional electrical elements; wherein the voltage source is configured to apply a first AC voltage under a first condition for actuating the microcantilever at a first mechanical resonating frequency of the microcantilever and a second AC voltage under a second condition for actuating the microcantilever at a second electrical resonating frequency of the resonating circuit. Method of using the sensor system is also described.

44 Claims, 12 Drawing Sheets

(51) Int. Cl.
  *G01G 3/16* (2006.01)
  *G01N 33/66* (2006.01)
  *G01N 33/543* (2006.01)

(52) U.S. Cl.
  CPC ....... *G01N 29/036* (2013.01); *G01N 33/5438* (2013.01); *G01N 2291/0257* (2013.01)

(58) Field of Classification Search
  USPC .......................................................... 73/579
  See application file for complete search history.

(56) References Cited

U.S. PATENT DOCUMENTS

| | | |
|---|---|---|
| 2007/0138909 A1 | 6/2007 | Mortet et al. |
| 2007/0169553 A1 | 7/2007 | Mutharasan et al. |
| 2010/0068697 A1 | 3/2010 | Shih et al. |
| 2011/0316386 A1* | 12/2011 | Karakaya ........... H03H 9/02259 310/318 |
| 2012/0094270 A1 | 4/2012 | Mutharasan et al. |

OTHER PUBLICATIONS

Faegh, et al., "Comprehensive Distributed-parameters Modeling and Experimental Validation of Microcantilever-based Biosensors with an Application to Ultrasmall Biological Species Detection," J. Micromech. Microeng., vol. 23, pp. 1-12 (2013).

Faegh, et al., "Ultrasensitive Piezoelectric-Based Microcantilever Biosensor: Theory and Experiment," IEEE/ASME Transactions on Mechatronics, vol. 20, No. 1, pp. 308-312 (Feb. 2015).

International Search Report and Written Opinion issued by the U.S. Patent and Trademark Office for International Application No. PCT/US2014/033287 dated Aug. 20, 2014 (9 pgs.).

Thaysen, et al., "Cantilever-based Bio-chemical Sensor Integrated in a Microliquid Handling System," The 14th IEEE International Conference on Micro Electro Mechanical Systems, Interlaken, Switzerland, pp. 401-404 (2001).

\* cited by examiner

SENSOR SYSTEM UTILIZING PIEZOELECTRIC MICROCANTILEVER COUPLED WITH RESONATING CIRCUIT

RELATED APPLICATIONS

This application is a national phase application, submitted under 35 U.S.C. § 371, of International Application No. PCT/US2014/033287, entitled "A NOVEL SENSOR SYSTEM UTILIZING PIEZOELECTRIC MICROCANTILEVER COUPLED WITH RESONATING CIRCUIT," filed on Apr. 8, 2014, which claims benefit of the earlier filing date of U.S. Provisional Patent Application No.: 61/809,734, entitled "NOVEL SENSOR SYSTEM UTILIZING PIEZOELECTRIC MICROCANTILEVER COUPLED WITH RESONATING CIRCUIT," filed on Apr. 8, 2013. All patents, patent applications and publications cited herein are hereby incorporated by reference in their entireties in order to more fully describe the state of the art as known to those skilled therein as of the date of the invention described herein.

BACKGROUND

Field of the Invention

The present disclosure relates to the field of sensor, specifically to a sensor system using a piezoelectric microcantilever coupled with a resonating circuit.

Description of Related Art

Development of nano- and micro-electromechanical systems (NEMS and MEMS) has been made possible due to advances in nanotechnology. Reducing the dimensions of electromechanical systems to micro- and nano-scale has enabled the identification of biological molecules utilizing mechanical biosensors. High-throughput diagnosis and analytical sensing require advanced biosensing tools exploiting high affinity of biomolecules. There are a number of useful biosensing techniques such as electrophoretic separation where spatiotemporal separation of analytes is possible. Another important technique is identifying the changes in the mass or optical properties of target proteins using spectrometric assays. Identification and quantification of target biomolecules due to high affinity which is based on molecular recognition has been known as one of the most reliable biosensing mechanisms.

There are two main elements in a biosensor which are i) sensitive biological receptor probe which interacts with target proteins and ii) transducer which transforms the molecular recognition into a detectable physical quantity. There are a number of instruments equipped with these elements developed for bio-detection such as quartz crystal microbalance (QCM), surface plasmon resonance (SPR), enhanced-Raman spectroscopy, field effect transistors (FET) and MicroCantilever (MC)-based biosensors. Among these techniques, MC-based biosensors have emerged as an outstanding sensing tool for being highly sensitive, label-free, and cost effective. All MC-based sensors are equipped with a read-out device which is capable of measuring the mechanical response of the system. There are a number of conventional read-out systems among which optical based measurement is the most commonly used. They have been widely used in atomic force microscopy (AFM) and measure the mechanical changes of the system by calculating the difference of the angle of laser beam reflected from the surface of the cantilever. Even though being sensitive, there are certain limitations with this technique which are mainly high cost, being bulky and surface preparation requirement. Moreover, laser alignment and adjustment and the requirement of the sample solution and liquid chamber to be transparent impose serious challenges for adopting such a method as a read-out device in molecular sensing tools.

There are two main operational modes of MC-based sensors which are i) static and ii) dynamic modes. Most of the studies regarding identification of molecular affinities have been performed in the static mode where the induced surface stress as a result of deflection of MC from a stable baseline to measure molecular binding. On the other hand, in dynamic mode, the system is brought into excitation at or near its resonance frequency. The shift in the resonance frequency as a result of molecular recognition yields a good insight into the amount of adsorbed mass.

One important factor determining the success of all biological sensors performing based on analytical sensing of high affinity of biomolecules is the ability of the sensor to operate in liquid media with high sensitivity. However, high dampening and viscous effects of solutions indeed impose a burden on the performance of biological sensor in a liquid environment. Some approaches have been developed to overcome this challenge by i) operating the system in humid gas-phase media, and ii) dipping the sensing probe in the solution, and then removing and desiccating it and finally doing the measurement. However these methods increase the interference of unspecific biomolecules, and prohibit real-time and continuous monitoring.

SUMMARY OF THE INVENTION

A sensor system using a self-sensing, interchangeable microcantilever and a method of using the sensor system in an interchangeable mode are provided.

In one aspect, a self-sensing, interchangeable sensor system is described, including: a microcantilever including a beam anchored at a first end, the beam being free to vibrate on another end; and a resonating circuit including a piezoelectric layer on a surface of the beam. The piezoelectric layer may act as a self-induced voltage source and a capacitor of the resonant circuit. The sensor system further includes an input to accept a voltage source for applying voltage to the piezoelectric layer; wherein the voltage source is configured to apply a first AC voltage under a first condition for actuating the microcantilever at a first frequency of the microcantilever and a second AC voltage under a second condition for actuating the beam at a resonating frequency of the resonant circuit. The first and the second AC voltages can have the same or different voltages. In some embodiments, the first and the second AC voltages have different frequencies. In some embodiments, the voltage source is part of the sensor system. In other embodiments, the sensor system includes an input configured to accept a voltage from the voltage source.

As used herein, the phrase "interchangeable sensor system" refers to a sensor system having an input to accept a voltage source capable of applying two voltages with two different frequency ranges to actuate the microcantilever at two different ranges of frequencies under two different conditions, i.e., the voltage source is configured to apply A) a first AC voltage under a first condition for actuating the microcantilever at a mechanically-resonating frequency of the microcantilever and B) a second AC voltage under a second condition for actuating the system at a resonating frequency of the resonant circuit. The interchangeable sensor system as described herein can easily switch between the voltages as required by the conditions without any modification to the sensor system. In some specific embodiments, the first and the second conditions correspond to the use of the sensor system in gaseous and liquid media, respectively. The liquid medium can be an aqueous medium.

As used herein, the phrase "self-sensing" refers to the ability of the piezoelectric layer to act as both the actuator of the beam movement and sensor for measuring the self-induced voltage generated by the beam movement. When subjected to voltage, the piezoelectric layer on a beam of the microcantilever may start resonating or vibrating, i.e., actuating the movement of the cantilever. At the same time, as a result of the vibration, the piezoelectric layer also generates a self-induced voltage which can be measured to extrapolate the intrinsic mechanical frequency information of the beam.

In an aspect of the present disclosure, a sensor system with a self-sensing, interchangeable microcantilever is provided. The microcantilever includes a beam anchored at a first end, the beam being free to vibrate on a second end, a piezoelectric layer on a surface of the beam, the piezoelectric layer configured to receive voltage from a voltage source, and a coating to immobilize receptors for binding with molecules. The system also includes a first capacitor in series with the piezoelectric layer, wherein a first trace between the piezoelectric layer and the capacitor includes a first electrical port, and two electrical elements in series arranged in parallel with the piezoelectric layer. The system further includes a first electrical element of the two electrical elements being a second capacitor and a third capacitor arranged in series with the two electrical elements and in parallel with the first capacitor. A second trace between the two electrical elements and the third capacitor includes a second electrical port, and the first electrical port and the second electrical port are configured to provide a self-induced voltage of the piezoelectric layer. The voltage source is configured to apply both A) a first AC voltage for actuating the microcantilever at a first resonating frequency of the microcantilever and B) a second AC voltage for actuating the microcantilever at a second resonating frequency of the resonating circuit, under different conditions.

In some embodiments, the mechanical resonating frequency of the microcantilever in a first medium, e.g., gas, without any molecule absorbed onto the beam is referred to as the first mechanical resonating frequency. In some embodiments, the mechanical resonating frequency of the microcantilever in the first medium, e.g., gas, with molecule absorbed onto the beam is referred to as the third mechanical resonating frequency. The frequency shift between these two frequencies can be analyzed to determine the amount or the nature of the molecule absorbed onto the beam in the first medium.

In some embodiments, the electrical resonating frequency of the resonating circuit in a second medium, e.g., liquid, without any molecule absorbed onto the beam is referred to as the second electrical resonating frequency of the resonating circuit. In some embodiments, the electrical resonating frequency of the resonating circuit in the second medium, e.g., liquid, with molecule absorbed onto the beam is referred to as the fourth electrical resonating frequency of the resonating circuit. The frequency shift between these two frequencies can be analyzed to determine the amount or the nature of the molecule absorbed onto the beam in the second medium.

In another aspect of the present disclosure, a method of detecting molecules is provided. The method includes applying, using the voltage source, one of the first AC voltage and the second AC voltage, immobilizing receptors on the coating of the microcantilever, the receptors for binding with molecules, and supplying molecules to the microcantilever. The method also includes, if the first AC voltage is applied, measuring i) a third mechanical resonating frequency of the microcantilever after the supply of the molecules, ii) a difference between the first and third mechanical resonating frequencies, and iii) an amount of molecules based on the difference between the first and third mechanical resonating frequencies. The method includes, if the second AC voltage is applied, measuring i) a fourth electrical resonating frequency of the resonating circuit after the supply of the molecules, ii) a difference between the second and fourth electrical resonating frequencies, and iii) an amount of molecules based on the difference between the second and fourth electrical resonating frequencies.

In one aspect, an interchangeable sensor system is described, including:
  a microcantilever including a beam anchored at a first end, the beam being free to vibrate on another end, wherein a piezoelectric layer is deposited on a surface of the beam;
  an input configured to receive a voltage from a voltage source for applying voltage to the piezoelectric layer; and
  a resonating circuit including:
    the piezoelectric layer, configured as a capacitor of the resonant circuit; and
    one or more additional electrical elements;
  wherein the voltage source is configured to apply a first AC voltage under a first condition for actuating the microcantilever at a first mechanical resonating frequency of the microcantilever and a second AC voltage under a second condition for actuating the microcantilever at a second electrical resonating frequency of the resonating circuit. The sensor system of claim 1, wherein under the first condition, the first AC voltage is applied with varying frequencies encompassing the first mechanical resonating frequency of the microcantilever.

In any of the preceding embodiments, the first AC voltage is applied with varying frequencies in the range of 1-1000 kHz.

In any of the preceding embodiments, under the second condition, the second AC voltage is applied with varying frequencies encompassing the second electrical resonating frequency of the resonant circuit.

In any of the preceding embodiments, the second AC voltage is applied with varying frequencies in the range of 1-20 MHz.

In any of the preceding embodiments, the sensor system is self-sensing and the piezoelectric layer is configured to act as a self-induced voltage source.

In any of the preceding embodiments, an arrangement of the voltage source, the piezoelectric layer, and one or more additional electrical elements is configured to implement the system in self-sensing, interchangeable mode.

In any of the preceding embodiments, the self-induced voltage is measured indirectly by measuring an output voltage of the circuit.

In any of the preceding embodiments, the sensor system further includes a detector configured to indirectly measure:
  the first mechanical resonating frequency of the microcantilever if the first AC voltage is applied under the first condition; and
  the second electrical resonating frequency of the resonant circuit if the second AC voltage is applied under the second condition.

In any of the preceding embodiments, the sensor system further includes coating on top of the piezoelectric layer configured to immobilize receptors for binding with molecules.

In any of the preceding embodiments, the one or more additional electrical elements include an inductor in parallel with the piezoelectric layer.

In any of the preceding embodiments, the one or more additional electrical elements include a first capacitor in series with the piezoelectric layer and a first trace between the piezoelectric layer and the first capacitor and including a first electrical port.

In any of the preceding embodiments, the resonating circuit further includes:
   two electrical elements in series arranged in parallel with the piezoelectric layer, wherein a first electrical element of the two electrical elements is a second capacitor; and
   a third capacitor arranged in series with the two electrical elements and in parallel with the first capacitor, wherein a second trace between the two electrical elements and the third capacitor includes a second electrical port.

In any of the preceding embodiments, the first electrical port and the second electrical port are configured to provide the self-induced voltage of the piezoelectric layer.

In any of the preceding embodiments, the first condition occurs when the microcantilever is in a gaseous medium, and the second condition occurs when the microcantilever is in a liquid medium.

In any of the preceding embodiments, the liquid medium is an aqueous medium.

In any of the preceding embodiments, the sensor system further includes a detector configured to detect a medium surrounding the microcantilever.

In any of the preceding embodiments, the sensor system further includes a detector configured to measure:
   a third mechanical resonating frequency of the microcantilever if the first AC voltage under the first condition is applied and the microcantilever are in contact with molecules; and
   a fourth electrical resonating frequency of the resonating circuit if the second AC voltage is applied under the second condition and the microcantilever are in contact with molecules.

In any of the preceding embodiments, the sensor system further includes a processor configured to measure a vibrational characteristic of the microcantilever.

In any of the preceding embodiments, the vibrational characteristic includes at least one of frequency and amplitude.

In any of the preceding embodiments, the one or more additional electrical elements include an inductor, capacitor, or resistor.

In any of the preceding embodiments, the molecules includes at least one of chemical compounds, vapors, organic materials, toxins, explosives, biological species, and DNA strands.

In any of the preceding embodiments, the coating includes gold.

In any of the preceding embodiments, the coating includes polymers.

In any of the preceding embodiments, the sensor system further includes a chamber covering at least part of the sensor system to expose the beam to a fluid.

In any of the preceding embodiments, the chamber includes Teflon.

In any of the preceding embodiments, the chamber is sealed.

In any of the preceding embodiments, the sensor system further includes an injection valve and syringe pump to operate and withdraw the fluid at a certain flow rate.

In any of the preceding embodiments, the beam includes one or more compounds selected from the group consisting of silicon and silicon compound.

In any of the preceding embodiments, the silicon compound includes silicon dioxide.

In any of the preceding embodiments, the piezoelectric layer includes zinc oxide.

In any of the preceding embodiments, the piezoelectric layer includes a piezoceramics material.

In any of the preceding embodiments, the piezoceramics material includes one or more materials selected from the group consisting of PZT and Aluminum Nitride.

In any of the preceding embodiments, the sensor system further includes a processor configured to measure an amount of molecules contacting the beam based on:
   the first mechanical resonating frequency if the first AC voltage is applied; and
   the second electrical resonating frequency if the second AC voltage is applied.

In any of the preceding embodiments, the step of measuring the amount of molecules includes solving an equation of motion of the system.

In another aspect, a method of detecting molecules is described, including:
   providing the sensor system of any one of the proceeding claims and a voltage source;
   applying, using the input to accept the voltage source, one of the first AC voltage under the first condition and the second AC voltage under the second condition to actuate the microcantilever;
   supplying molecules to the microcantilever;
   if the first AC voltage is applied, measuring i) a third mechanical resonating frequency of the microcantilever after the supply of the molecules, ii) a difference between the first and third mechanical resonating frequencies, and iii) an amount of molecules based on the difference between the first and third mechanical resonating frequencies; and
   if the second AC voltage is applied, measuring i) a fourth electrical resonating frequency of the resonating circuit after the supply of the molecules, ii) a difference between the second and fourth electrical resonating frequencies, and iii) an amount of molecules based on the difference between the second and fourth electrical resonating frequencies.

In any of the preceding embodiments, the method further includes applying as a coating on top of the piezoelectric layer configured to bind the molecules.

In any of the preceding embodiments, the voltage source applies the first AC voltage when the microcantilever is in a gaseous medium, and wherein the voltage source applies the second AC voltage when the microcantilever is in an aqueous medium.

In any of the preceding embodiments, the method further includes detecting a surrounding medium of the microcantilever.

In any of the preceding embodiments, the step of detecting the medium includes applying a third voltage using the voltage source and determining the surrounding medium based on a movement of the microcantilever.

In any of the preceding embodiments, the method further includes performing a Fast Fourier Transform to determine a resonance frequency of the microcantilever.

In any of the preceding embodiments, the method further includes applying an immobilizing receptor to the coating, the immobilizing receptor designed to immobilize molecules over the coating.

In any of the preceding embodiments, the receptor includes an aminoethanethiol.

In any of the preceding embodiments, the step of measuring the amount of molecules includes solving an equation of motion of the system.

DETAILED DESCRIPTION OF THE INVENTION

Figure 1:
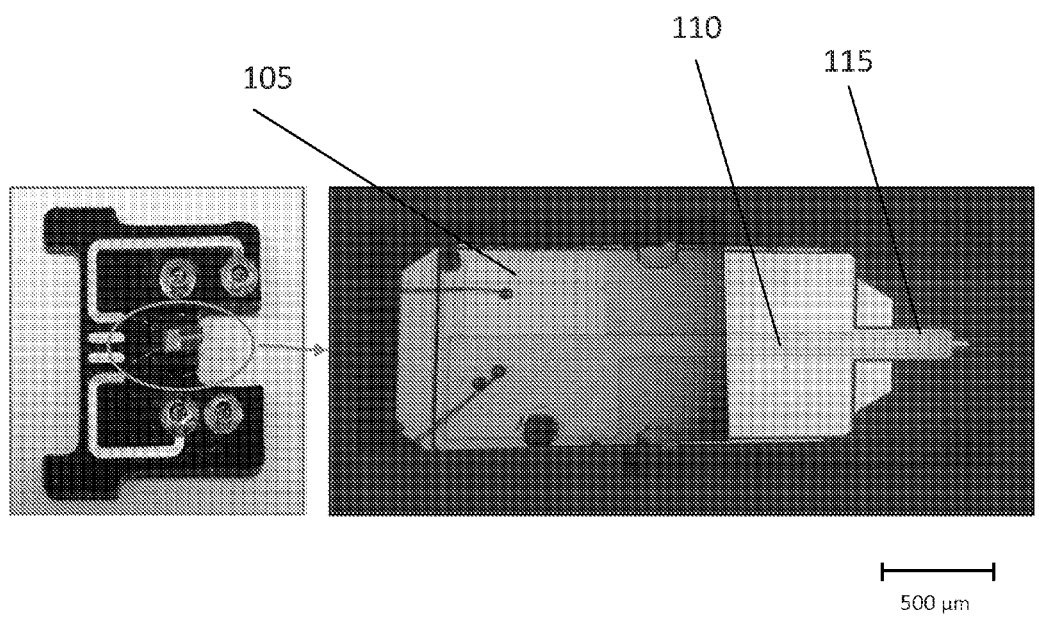
FIG. 1 illustrates a self-sensing microcantilever in accordance with embodiments of the present disclosure.

A sensor system using a piezoelectric microcantilever and a resonating circuit is provided. The microcantilever includes a beam with a piezoelectric layer on the surface of the beam. The beam is anchored at a first end and is free to vibrate on another end. The resonating circuit includes the piezoelectric layer on a surface of the beam. The piezoelectric layer may act as a self-induced voltage source and a capacitor of the resonant circuit. The sensor system further includes a voltage source for applying voltage to the piezoelectric layer and one or more additional electrical elements. The voltage source, the piezoelectric layer, and one or more additional electrical elements are arranged to implement the system in the self-sensing mode.

In some embodiments, the system is implemented in A) Mechanical mode (for gaseous media): where the AC voltage is swept at a range of frequency encompassing the microcantilever's mechanical fundamental resonance frequency; and B) Electrical mode (for aqueous media): where the AC voltage is swept at a range of frequency encompassing circuits resonance frequency. The output voltage of the circuit (306, FIG. 3) in both conditions (A) and (B) is measured before and after supplying molecules over the microcantilever surface, where the shift in the resonance frequency of the measured voltage (306, FIG. 3) can be correlated to the amount of supplied molecules.

The sensor system described herein takes advantage of the two distinct frequencies of the sensor system including the microcantilever and the resonating circuit. Specifically, the sensor system has a input configured to accept a voltage from a voltage source which is configured to apply a voltage to cause the microcantilever to vibrate at its fundamental mechanical resonance frequency (a lower frequency) under a first condition, e.g., in a gas medium. Alternatively, the voltage source may apply a higher-frequency voltage in the circuit's electrical resonance frequency under a second condition, e.g., in a liquid medium. In some embodiments, the lower-frequency and the higher frequency voltages are sinusoidal voltages. The sensor system can easily switch between the two different frequencies without any modification to the system. As a result, a single sensor system described herein can be conveniently and efficiently used in multiple media, which simplifies the detection equipment one has to use.

In some embodiments, the mechanical resonance frequency is much lower than the resonating circuit's frequency. Specifically, under the first condition, the first AC voltage can be applied with varying frequencies encompassing or close to the first mechanical resonating frequency of the microcantilever to actuate the mechanical resonance of the microcantilever. In some embodiments, the first AC voltage's varying frequencies is in the range of 1-1000 kHz, 10-1000 kHz, 100-1000 kHz, 200-1000 kHz, 500-1000 kHz, 1-500 kHz, 10-500 kHz, 100-500 kHz, 1-100 kHz, or 10-100 kHz.

In some embodiments, under the second condition, the AC voltage is applied with varying frequencies encompassing or close to the second resonating frequency of the resonant circuit (as opposed to a first, mechanical resonating frequency). In some embodiments, the second AC voltage's varying frequencies is in the range of 1-20 MHz, 2-20 MHz, 3-20 MHz, 4-20 MHz, 5-20 MHz, 6-20 MHz, 7-20 MHz, 8-20 MHz, 9-20 MHz, 10-20 MHz, 1-10 MHz, 2-10 MHz, 3-10 MHz, 4-10 MHz, 5-10 MHz, 6-10 MHz, 7-10 MHz, 8-10 MHz, 9-10 MHz, 1-5 MHz, 2-5 MHz, 3-5 MHz, 4-5 MHz, 1-4 MHz, 2-4 MHz, 3-4 MHz, 1-3 MHz, or 1-2 MHz.

The suitable frequencies used by the sensor system described herein are not limited to the frequencies described above. In some embodiments, the frequencies used by the sensor system described herein are compatible with the signal processing hardware used in the sensor system.

The sensor system uses both direct and inverse properties of a piezoelectric material to play the role of both sensor and actuator. A direct piezoelectric property is used to sense the self-induced voltage generated in the piezoelectric layer as a result of beam deformation. An inverse property of piezoelectric material is used to generate deformation and bring the system into vibration as a result of applying a sinusoidal voltage to the piezoelectric layer.

A voltage source can apply two distinct resonating voltages for two approaches of mass detection. First, the voltage source may apply a lower frequency sinusoidal voltage to cause the microcantilever to vibrate at its mechanical resonance frequency. The application of low frequency sinusoidal voltage can be used for detecting molecules in gas. Second, the voltage source may apply a higher sinusoidal voltage in the circuit's electrical resonance frequency. This use of circuit's electrical resonance frequency can aid detecting molecules in liquid.

As described above, the microcantilever has a characteristic mechanical resonance frequency (a lower frequency) which will change upon the contact or absorption of molecules on the surface of the beam. A measurement of this frequency change can be used to determine the amount or character of the molecules on the surface of the beam. This frequency can be measured using a detector, e.g., the output voltage of the system (306 of FIG. 3). In some embodiments, the voltage source may apply a sinusoidal voltage to determine the characteristic frequencies described here, e.g., the mechanical resonating frequency of the microcantilever or the electrical resonating frequency of the resonant circuit.

On the other hand, the resonating circuit of the sensor system has a unique electrical resonance frequency. The contacts of molecules with the piezoelectric layer (e.g., binding of molecules onto the beam of the microcantilever or onto the coating of the microcantilever), which is a part of the resonating circuit and acts as a capacitor in the resonating circuit, will change the capacitance of the piezoelectric layer and, in turn, the electrical resonance frequency of the resonating circuit. Thus, a measurement of the electrical resonance frequency change can be used to determine the amount or character of the molecules on piezoelectric layer on the surface of the beam as well.

The use of the electrical resonance frequency, which changes upon molecular binding, has further advantages when used in liquid medium. The method of using mechanical resonance frequencies of the MC may not be effective for detecting molecules in a liquid environment due to high viscoelastic damping and losses in the surrounding liquid. However, unlike the mechanical responses, the electrical response, e.g, the measurement of the electrical resonance frequency, does not diminish with high viscoelastic damping. Thus, the measurement of the electrical resonance frequency change can result in more accurate reading of the molecular binding onto the surface of the microcantilever. In fact, the mechanical frequencies in the liquid medium will be nearly completely offset by the damping effect of the liquid. As a result, the intrinsic frequency of the microcantilever measured in the liquid will be solely the intrinsic frequency of the resonating circuit and free from any contribution of the mechanical frequency of the microcantilever.

In some embodiments, the beam of the microcantilever can be chemically modified. In some embodiments, the chemical modification includes a coating applied on the piezoelectric layer. The chemical modification of the beam will result in the specific binding of the target molecule onto the beam. In some embodiments, the coating includes gold. In other embodiments, the coating includes polymers. However, any coating of compound known to increase the specific absorption or binding of a target molecule can be used.

In yet another embodiment, an immobilizing solution is applied to the coating. The immobilizing solution can be designed to immobilize molecules over the coating. The receptor can include an aminoethanethiol. The step of measuring the amount of molecules can include correlating motion (e.g., frequency) of the system to the composition and/or load of a selected molecule on the cantilever beam.

Figure 3:
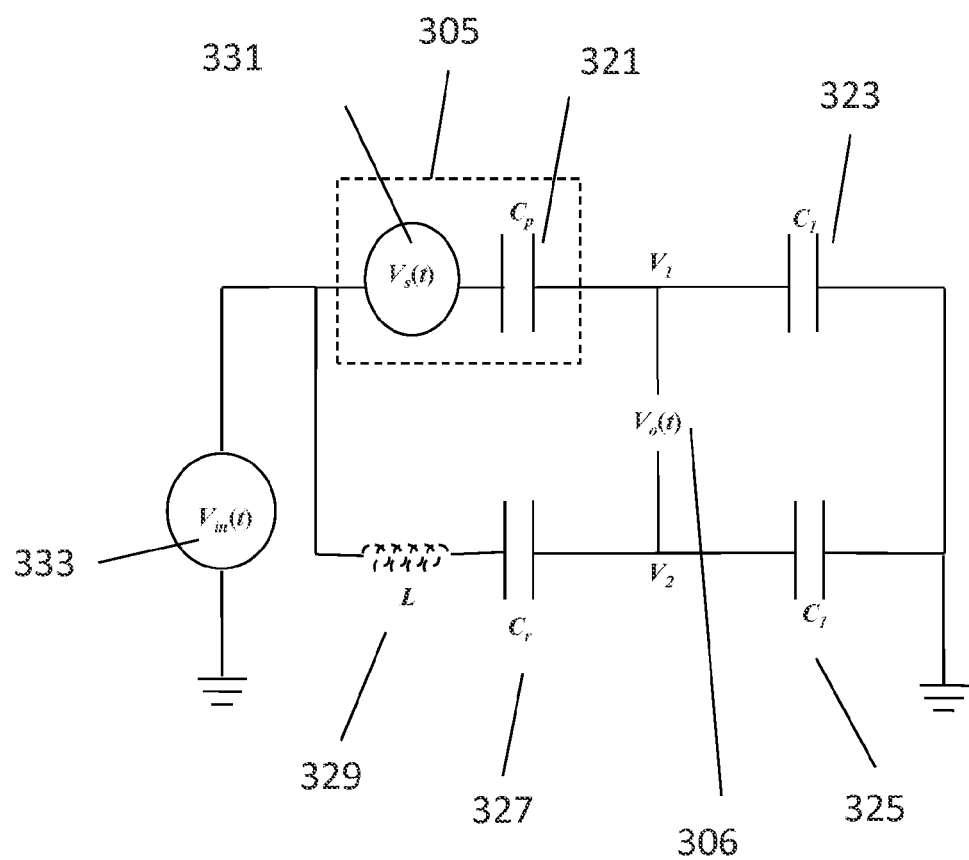
FIG. 3 illustrates a schematic circuit diagram of a sensor system using a microcantilever in accordance with embodiments of the present disclosure.

In one embodiment, the resonating circuit is configured as shown in FIG. 3. However, any resonating circuit may be used in the sensor system described herein. The resonating circuit includes at least an inductor (L), and a capacitor (C). In the resonating circuit, resonance occurs at a particular frequency when the inductive reactance and the capacitive reactance are of equal magnitude, causing electrical energy to oscillate between the magnetic field of the inductor and the electric field of the capacitor. Resonance occurs because the collapsing magnetic field of the inductor generates an electric current in its windings that charges the capacitor and the discharging capacitor provides an electric current that builds the magnetic field in the inductor. In some embodiments, the resonating circuit includes the piezoelectric layer (providing capacitance) and a balancing bridge (providing inductance). The bridge may include an inductor and/or capacitor. In some embodiments, the resonating circuit has a high quality factor.

The quality factor of the resonating circuit refers to the ratio of stored energy/dissipated energy of the resonating circuit. High quality factor resonating circuit results in higher amplitude in resonant frequency with a smaller bandwidth indicating lower damping effect thus lower rate of energy loss compared to resonating circuit's stored energy. In some embodiments, the quality factor of the resonating circuit is more than about 10, 50, 100, 200, 300, 400, 500, or 1000. In some embodiments, the quality factor of the resonating circuit is form about 10 to about 1000. In some embodiments, the quality factor of the resonating circuit is form about 100 to about 500. In some embodiments, the quality factor of the resonating circuit is form about 100 to about 3000.

The sensor system may further include one or more additional electrical elements. Non-limiting examples of the additional electrical element includes inductor and capacitor and resistor.

In some embodiments, a sensor system with a self-sensing, interchangeable microcantilever and a resonating circuit is described with reference to FIG. 3 on the circuit level. The microcantilever includes a beam anchored at a first end, the beam being free to vibrate on a second end, a piezoelectric layer on a surface of the beam, the piezoelectric layer configured to receive voltage from a voltage source, and a coating to immobilize receptors for binding with molecules. The piezoelectric layer is shown as part of the circuit in the dash-line box in FIG. 3 as a self-induced voltage (331) source and a cantilever capacitor (321) of the resonant circuit. The system also includes a first capacitor (323) in series with the piezoelectric layer. A first trace between the piezoelectric layer and the capacitor includes a first electrical port that provides voltage readout that correlates to the self-induced voltage of the piezoelectric layer. The system also includes two serially connected electrical elements (327 and 329), which are arranged in parallel with a self-induced voltage (331) source and a cantilever capacitor (321) of the piezoelectric layer. As shown in FIG. 3, the first electrical element of the two electrical elements is a second capacitor (327) and the second electrical element (329) can be an inductor. A third capacitor (325) is arranged in series with the two electrical elements and in parallel with the first capacitor (323). Any other configuration of the circuit can be used as long as it can be implemented as a resonating circuit with high quality factor. A voltage source (333) is applied to the resonating circuit including the piezoelectric layer 305. In response, the piezoelectric layer generates a self-induced voltage 331. The self-induced voltage 331 can be indirectly measured by measuring output voltage 306. The output voltage related to self-induced voltage through comprehensive mathematical modeling of the system, through the mechanical resonating frequency of the beam or the electrical resonating frequency of the resonating circuit can be derived. The voltage source (333) is configured to apply both A) a first AC voltage for actuating the microcantilever at a first fundamental or mechanical resonating frequency of the microcantilever and B) a second AC voltage for actuating the microcantilever at a second resonating frequency of the resonating circuit, under different conditions.

Additional embodiments of the sensor system are provided. The voltage source can apply the first AC voltage under the first condition when the microcantilever is in a gaseous medium, and the voltage source can apply the second AC voltage under the second condition when the microcantilever is in an aqueous medium. The system can also include a detector configured to detect a medium surrounding the microcantilever. The system can also include a detector configured to measure an output third resonating frequency of the microcantilever if the first AC voltage is applied under the first condition and an output fourth resonating frequency of the resonating circuit if the second AC voltage is applied under the second condition. In some embodiments, the third and fourth resonating frequencies are measured or derived from the output voltage (e.g., FIG. 3, 306).

In another embodiment, the piezoelectric coating is capable of immobilizing a variety of molecules, such as at least one of chemical compounds, vapors, organic materials, toxins, explosives, biological species, and DNA strands.

In yet another embodiment, the coating can include gold, or the coating can include polymers.

In a further embodiment, the sensor system can include a chamber covering the beam. The chamber can include Teflon. The chamber can be sealed. The sensor system can also include an injection valve and syringe pump to operate and withdraw the fluid (gas or liquid) at a certain flow rate.

The beam is rigid, yet capable of deflection when subjected to an external force, e.g., a tensile force. In one embodiment, the beam includes at least one of silicon and silicon compound. The silicon compound includes silicon dioxide. The piezoelectric layer can include any known piezoelectric material, and in particular can include a piezoelectric material capable of exhibiting mechano-electrical resonance within a range (e.g., frequency range) suitable for use as a resonance component of the system. The piezoelectric layer can also include a piezoceramics material. The piezoceramics material can include at least one of zinc oxide. lead zirconate titanate (PZT) and Aluminum Nitride.

In another embodiment, the system can include a detector configured to measure an amount of molecules based on the first mechanical resonating frequency if the first AC voltage is applied under the first condition and the second electrical-resonating frequency if the second AC voltage is applied under the second condition. The step of measuring the amount of molecules can include correlating motion (e.g., frequency) of the system to the composition and/or load of a selected molecule on the cantilever beam.

In another aspect of the present disclosure, a method of detecting molecules is provided. The method includes applying, using the voltage source described herein, one of the first AC voltage and the second AC voltage to actuate the microcantilever, under the first and second conditions, respectively; supplying molecules to the microcantilever. If the molecules bind to receptors on the functionalized microcantilever beam, the frequency of oscillation will change, and the new frequency can provide information regarding the composition and/or concentration of a target molecule.

The method also includes, if the first AC voltage is applied under the first condition, measuring i) a third mechanical resonating frequency of the microcantilever after the supply of the molecules, ii) a difference between the first and third mechanical resonating frequencies, and iii) determining an amount of molecules based on the difference between the first and third mechanical resonating frequencies. The method includes, if the second AC voltage is applied under the second condition, measuring i) a fourth electrical resonating frequency of the resonating circuit after the supply of the molecules, ii) a difference between the second and fourth electrical resonating frequencies before and after supplying molecules, and iii) determining an amount of molecules based on the difference between the second and fourth electrical resonating frequencies. In some embodiments, the method further includes applying as a coating on top of the piezoelectric layer configured to bind the molecules.

In an embodiment, the voltage source can apply the first AC voltage under the first condition when the microcantilever is in a gaseous medium, and the voltage source can apply the second AC voltage under the second condition when the microcantilever is in an aqueous medium. The method can also include detecting a surrounding medium of the microcantilever. The movement of the microcantilever can be measured by the output voltage based on the movement of the beam and the resulting self-produced voltage generated.

In another embodiment, the method can include determining a resonance frequency of the microcantilever. Non-liming examples of determining the resonance frequency include using a detector or software such as Metlab to perform a Fast Fourier Transform.

In yet another embodiment, the method includes applying an immobilizing solution to the coating. The immobilizing solution can be designed to immobilize molecules over the coating. The receptor can include an aminoethanethiol. The step of measuring the amount of molecules can include correlating motion (e.g., frequency) of the system to the composition and/or load of a selected molecule on the cantilever beam.

Microcantilever

FIG. 1 illustrates a microcantilever 101 of the sensor system. The microcantilever 101 includes a beam 115 and a piezoelectric layer 110. The beam 115 can be made of silicon, silicon compounds (e.g, silicon dioxide), or other materials with good yield strength and modulus of elasticity. Silicon is widely used because the overall properties of silicon are very good at small scales. Combination of the yield strength and modulus of elasticity (among other properties) of silicon is especially useful for the life and durability of small devices. Some other materials, such as silicon carbide or diamond, offer better properties, but they also cost many times more than silicon making them uneconomical except for the most demanding and specific purposes. (See Thaysen et al., *Cantilever-based bio-chemical sensor integrated in a microliquid handling system*. Technical Digest. MEMS 2001) This crystallographic orientation of silicon may allow MEMS to have well defined and sharp edges and shapes with perpendicular angles resulting from etching. Materials that are elastic with a small spring constant can be useful because it results in a large bending amplitude.

The microcantilever, as shown in FIG. 1, can be a commercially available probe (e.g., Veeco Active Probe). Veeco Active Probe already comes with a piezoelectric layer, or piezoelectric material can be deposited on the beam when there is no pre-assembled parts. The piezoelectric material can be a Zinc Oxide (ZnO). Alternatively, any other piezoelectric material with high crystallographic asymmetry which consequently results in high stiffness and electromechanical coefficient can be used. Some examples of such materials are piezoceramics (e.g., PZT, Aluminum Nitride, etc.).

Figure 2A:
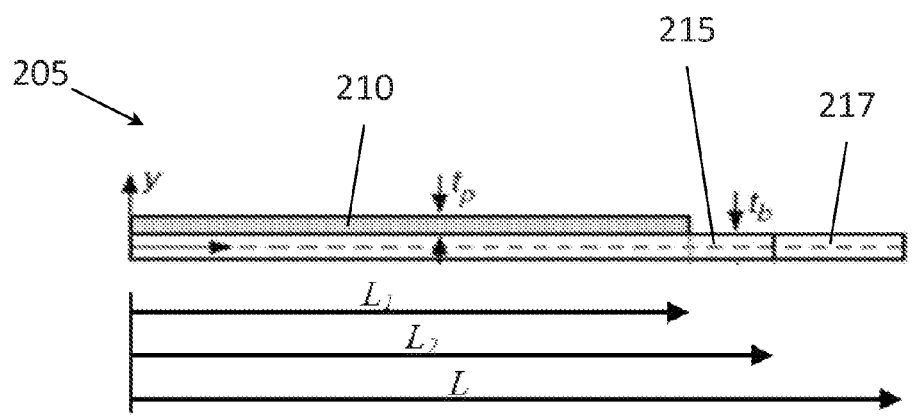
FIG. 2A illustrates a side view of the microcantilever in accordance with embodiments of the present disclosure.
Figure 2B:
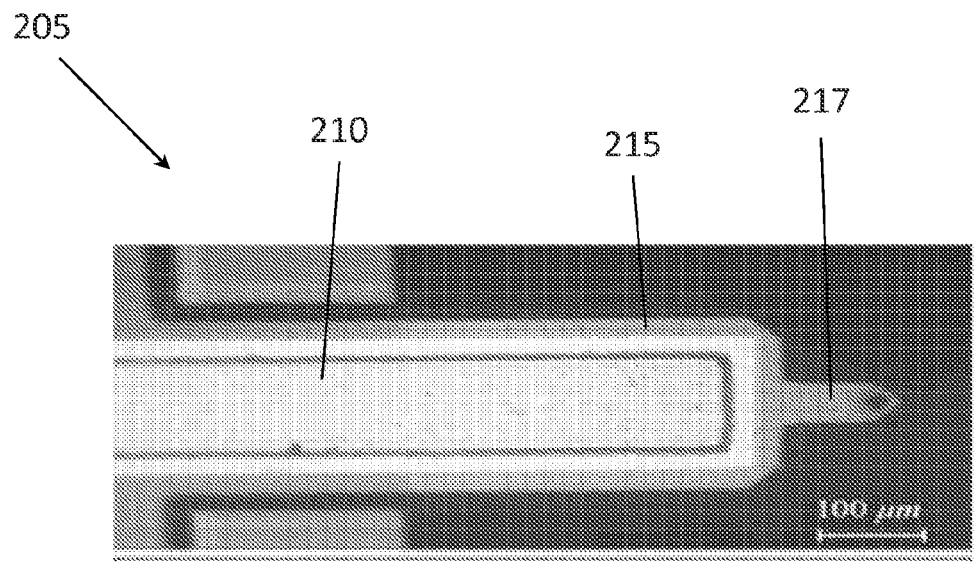
FIG. 2B illustrates an upper view of the microcantilever in accordance with embodiments of the present disclosure.

FIG. 2A illustrates a side view of the microcantilever 201, including a beam 215 and a piezoelectric layer 210. The beam 215 is fixed on one end and has a tip 217 on the other end. The main portion of the beam 215 has a length $L_2$, and the piezoelectric layer has a length $L_1$. The full length of the beam including its tip is L. The thickness of the piezoelectric layer is $t_p$ and the thickness of the beam is $t_b$. The dimension is not limited to what is presented, but can vary based on its application and manufacturing method. FIG. 2B illustrates a top-down view of the microcantilever 201. The MC beam can be narrowed at the tip which can add to the sensitivity of the system. The change in the cross-section at the tip results in less rigidity around this area, which in turn produces more flexibility, more vibration, and hence more sensitive readout measurement. In some embodiments, only the coated section (0–$L_1$, FIG. 2A) of the beam is functionalized. The use of the narrow tip can increase sensitivity and result in easier detection of the movement the beam.

The system with the microcantilever can be used for detection of, for example, chemical compounds, vapors, organic materials, toxins, explosives, biological species, and DNA strands. As a disease diagnosis platform, the system can enable detection of any type of disease marker proteins and analysis of gene expression at the genomic and proteomic level. As an environmental sensor, the system can enable detection of toxic chemicals and biological agents. Screening potential environmental contaminants, such as endocrine disrupting chemicals or detection of microbial pathogens in water and other environmental samples, would have a great impact in monitoring and saving environmental resources. As a gas sensor, the system can enable screening high explosive gases and toxic chemicals. Detecting tiny masses in air and differentiating particles based on a signature would be revolutionary since current real time instrumentation cannot differentiate between engineered and incidental nanoparticles.

The microcantilever can be coated using a suitable material for the particular detection purpose. For example, the microcantilever can be coated with gold when used as a biosensor, because gold can immobilize receptor biomolecules. As a gas sensor, the microcantilever may use a polymer coating for detection of different vapors. Any material that swells when exposed to vapor, e.g. hydrogels, can serve the purpose.

An active surface of the microcantilever can be functionalized. For a biosensor example, the active surface, which is the extended electrode coated with gold, can be functionalized by an enzyme layer. The gold coating can be employed for immobilizing the GoX enzyme, which is itself a receptor for biomolecules such as Glucose. The biosensor example is further discussed in a later section describing experiments.

In a gaseous environment, the ultrasmall masses that are functionalized over a MC surface can be detected through a self-sensing circuit by measuring a deflection (in a static mode) or a shift in the first or higher mechanical resonance frequencies (in a dynamic mode) of the MC. The method of using mechanical resonance frequencies of the MC is described in detail in Faegh, S.; Jalili, N.; Sridhar, S., *Ultrasensitive Piezoelectric-Based Microcantilever Biosensor: Theory and Experiment*, IEEE/ASME Transactions on Mechatronics, vol.PP, no. 99, pp. 1-5, which is incorporated herein by reference.

However, this method of using mechanical resonance frequencies of the MC may not be effective for detecting marker proteins in a liquid environment due to high viscoelastic damping and losses in the surrounding liquid. Unlike the mechanical responses, the electrical response does not diminish with high viscoelastic damping. Output voltage of the circuit is measurable no matter the sensing element is in aqueous and gaseous media, thereby enabling measurement of the resonance of the whole circuit instead of mechanical resonance which is difficult to measure in liquids. Therefore, in liquid media, molecules are detected by measuring a shift in an electrical resonance frequency of the circuit. Therefore, by utilizing the two different frequencies, i.e., the mechanical resonance frequency of the MC and the electrical resonance frequency of the circuit, the sensor system as disclosed herein can be used in both gas and liquid medium.

In some embodiments, for the detection of molecules in both gas and liquid, two sensors may be used. One sensor uses an unfunctionalized microcantilever for a reference sensor, and the other sensor uses a functionalized microcantilever. Molecules bind to the functionalized microcantilevers and not to the unfunctionalized microcantilever. After detecting the shifts in resonance frequencies of both microcantilevers, the difference in the frequency shifts can be measured. The differential shift provides more accurate and reliable results regardless of the surrounding media by cancelling out or reducing the effects of the unspecific interferences, background and environmental noises. Thus, measuring the differential response between the sensor MC and the reference MC (instead of purely measuring the sensor response), allows for compensating for the unwanted interferences and results in more accurate results.

The appropriate sinusoidal voltage can be applied manually. For example, an operator determines the surrounding medium and selects the right voltage. Alternatively, the voltage can be chosen automatically by automatic detection of the surrounding medium. The system can have a separate detector detecting the surrounding medium in which the microcantilever is placed or detect the medium based on the response of the microcantilever. For example, the system can adjust the frequency range and actuate the microcantilever while simultaneously measuring the response using the same piezoelectric element on the micocantilever.

Beam—Mathematical Modeling

The present disclosure provides a comprehensive mathematical modeling using a distributed-parameters model. The mathematical model for the microcantilever in the dynamic mode can be constructed using various techniques, including the Euler-Bernoulli beam theory. The Euler-Bernoulli beam theory models the current system with a high level of accuracy. Alternatively, the beam can be modeled as a nonuniform rectangular plate. The method of modeling a beam is described in detail in Faegh et al., *Comprehensive distributed-parameters modeling and experimental validation of microcantilever-based biosensors with an application to ultrasmall biological species detection*, 2013 J. Micromech. Microeng. 23, pp 1-12, which is incorporated herein by reference.

The self-sensing model can be implemented through a piezoelectric layer mounted on the base of the probe extending close to the tip as shown in FIGS. 2A-B. For the piezoelectric material, ZnO can be used. The MC beam is modeled as a non-uniform cross-section beam with the total length of L and an active length (piezoelectric layer) of $L_1$ which is used for functionalization. The beam is considered to have thickness $t_b$, and volumetric density $\rho_b$. The piezoelectric layer over the top surface of the cantilever has thickness $t_p$, and volumetric density $\rho_p$. Both MC beam and piezoresistive layer are considered to have width b.

The dimensions and other design parameters described above are non-limiting examples. The mathematical model can be designed with other parameters. For example, the width of the beam and the piezoresistive layer can be different. The tip of the beam does not have to be narrower than the body of the beam. The beam can be modeled with a uniform cross section beam.

w(x,t) denotes the midplane deflection of MC beam with the tip deflection as w(L,t). Small deflection and linear system properties assumptions are taken into account. The equation of motion of the system is derived using Extended Hamilton's principle. The system is typically actuated by applying a resoanting sinusoidal voltage to the piezoelectric layer.

The following distributed-parameters modeling is proposed for the response of the system to the applied input. For this, the kinetic energy of the system is written as $$KE = \frac{1}{2}\int_0^L \rho(x)\left[\frac{\partial w(x,t)}{\partial t}\right]^2 dx \tag{1}$$

where $$\rho(x) = \rho A(x) = \rho_b b t_b + \rho_p b t_p G(x) \tag{2}$$

with $G(x)=1-H(x-L_1)$, and $H(x)$ being the Heaviside function. Considering that beam only extends in the x-direction, potential energy of the system is written as $$\delta PE = \int_0^L \sigma_x \delta \epsilon_x dx \tag{3}$$

in which the stress-strain relationship for beam and piezoelectric layer can be obtained from $$\sigma_x^b = E_b \epsilon_x \tag{4}$$

$$\sigma_x^p = E_p \epsilon_x + E_p d_{31} \frac{V(t)}{t_p} \tag{5}$$

with $E_b$ and $E_p$ being beam and piezoelectric elastic moduli, respectively. V(t) is the applied input voltage to the system, and $d_{31}$ is the piezoelectric constant. Strain in the x-direction is related to the transverse deflection of the beam by $$\epsilon_x = -y\frac{\partial^2 w(x,t)}{\partial x^2}$$

which should be modified as $$\epsilon_x = -(y-y_n)\frac{\partial^2 w(x,t)}{\partial x^2}$$

when used for the piezoelectric section as a result of shift in the neutral axis. This shift $y_n$ can be expressed as $$y_n = \frac{E_p t_p (t_p + t_b)}{2(E_p t_p + E_b t_b)} \tag{6}$$

Therefore, the virtual potential energy can be rewritten as $$\delta PE = \int_0^L \frac{\partial^2}{\partial x^2}\left[EI(x)\frac{\partial^2 w(x,t)}{\partial x^2}\right]dx + M_{p0}V(t)\int_0^{L_1}\frac{\partial^2 G(x)}{\partial x^2}dx \tag{7}$$

where $M_{p0}$ is defined as $$M_{p0} = bE_p d_{31}\left[\frac{1}{2}(t_b + t_p) - y_n\right] \tag{8}$$

The varying stiffness of the system EI(x) is $$EI(x) = E_b I_b(x) + E_p I_p(x) \tag{9}$$

$$I_b(x) = \frac{1}{12}bt_b^3 + G(x)bt_b y_n^2$$

$$I_p(x) = \left[\frac{1}{12}bt_p^3 + bt_p y_n^2\left(\frac{1}{2}(t_b+t_p)-y_n\right)^2\right]bG(x)$$

The virtual work due to ever-present viscous and structural damping terms is given by $$\delta W = \int_0^L (-B\dot{w}(x,t) - C\dot{w}'(x,t))\delta w(x,t)dx \tag{10}$$

where B and C represent the coefficients of viscous and structural damping, respectively. ( )' is partial derivative with respect to spatial coordinate x, while ( ̇) denotes temporal derivative. Using Extended Hamilton's principle, the equations of motion of the system can be obtained as $$\rho(x) = \frac{\partial^2 w(x,t)}{\partial x^2} + \frac{\partial^2}{\partial x^2}\left[EI(x)\frac{\partial^2 w(x,t)}{\partial x^2}\right] + B\frac{\partial w(x,t)}{\partial t} + C\frac{\partial^2 w(x,t)}{\partial x \partial t} = -M_{p0}V(t)G''(x) \tag{11a}$$

with the boundary conditions $$w(0,t)=w'(0,t)=0 \tag{11b}$$

$$w''(L,t)=w'''(L,t)=0 \tag{11c}$$

The step of calculating the applied voltage to the system, V(t), is based on the voltage source-supplied voltage, $V_c(t)$ and the self-induced voltage, $V_s(t)$.

In some embodiments of the present disclosure, the obtained governing equations of motion (Eq. 11) can be discretized and solved using Galerkin's method. The equation can also be solved using other numerical methods, including Boundary Element Method, Finite Volume Method, and Finite Difference Method. The partial differential Equation (11) can be converted into ordinary differential equation (ODE) using the following discretization $$w(x,t) = \sum_{j=1}^{n} \varphi_j(x) q_j(t), j=1,2,\ldots,n \qquad (12)$$

with $\varphi_j(x)$ and $q_j(t)$ being the clamped-free beam eigenfunction and generalized coordinates, respectively. Therefore, the equation of motion can be expressed as a function of time in a matrix form. The ODE for the system can be then represented as $$M\ddot{q}(t) + D\dot{q}(t) + Kq(t) = K_v V(t) \qquad (13)$$

where $$q = \{q_1, q_2, \ldots q_i\}, \dot{q} = \{\dot{q}_1, \dot{q}_2, \ldots \dot{q}_i\} \qquad (14)$$

$$M = \{M_{ij}\}, M_{ij} = \int_0^L \rho A(x) \phi_j(x) \phi_i(x) dx,$$

$$i, j = 1, 2, \ldots, n$$

$$D = \{D_{ij}\}, D_{ij} = B \int_0^L \phi_j(x)\phi_i(x) dx + C \int_0^L \phi'_j(x)\phi_i(x) dx$$

$$K = \{K_{ij}\},$$

$$K_{ij} = \int_0^L EI(x)\phi''_j(x)\phi''_i(x) dx -$$

$$\frac{M_{P0}}{C_1 + C_p} K_s [\phi'_j(L_1) - \phi'_j(0)][\phi'_i(L_1) - \phi'_i(0)]$$

$$K_v = \{K_{vj}\},$$

$$K_{vj} = -M_{p0} \int_0^L \phi'_j(x)\delta(x - L_1) dx = -M_{p0}\phi'_j(L_1)$$

Resonating Circuit

A resonating circuit can be used to apply the voltage to self-sensing MC. The Voltage source can be any device capable of producing voltage in the range of frequencies that is desired for the purpose of this work. The produced voltage may be represented by 333 in FIG. 3. The circuit's resonance frequency and the shift of the resonance frequency as a result of the change in the capacitance due to molecular binding provides information about the molecules. For example, the resonance frequency of the circuit can be measured while operating the system in liquid, therefore allowing for rapid, continuous, and highly sensitive measurement of molecular recognition.

Figure 4:
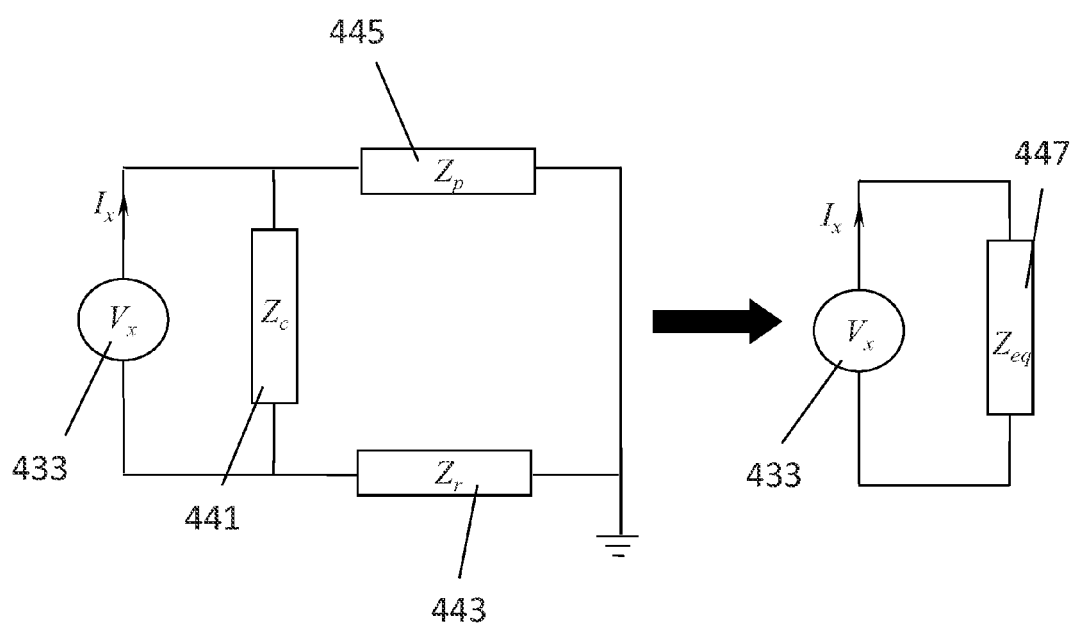
FIG. 4 illustrates a circuit diagram to find equivalent impedance in accordance with embodiments of the present disclosure.

In order to find the equivalent impedance of the circuit from the output port, the circuit shown in FIG. 3 is turned into the following circuit (FIG. 4): $V_x$ (433) being an imaginary source of voltage, $Z_c$ (441) the impedance as a result of induced stray capacitance ($C_c$) and resistance ($R_c$) from the connecting cable, $Z_p$ (445) and $Z_r$ (443), the impedance resulting from other elements of the circuit including capacitors ($C_1$, and $C_r$) and inductor (L). Each of these impedances can be calculated as follows:

$$z_p = \frac{1}{C_1 wj + C_p wj} \qquad (15)$$

$$z_r = \frac{1}{C_1 wj + \frac{1}{\frac{1}{C_r wj} + Lwj}} \qquad (16)$$

$$z_c = \frac{1}{\frac{1}{R_c} + C_c wj} \qquad (17)$$

$$z_{eq} = \frac{1}{\frac{1}{z_c} + \frac{1}{z_p + z_r}} \qquad (18)$$

with w being the frequency of the circuit. Based on the above equations, $Z_{eq}$ (447) can be calculated, which is a complex function. Setting the imaginary part of $Z_{eq}$ to zero, the following equation is obtained:

$$[AF+EB] \times [CG-DH] - [AE-FB] \times [CH+DG] = 0 \qquad (19)$$

where $A = -C_1 R_c w - R_c(C_1+C_p)w + [1-C_1 L w^2]wC_c R_c^2 - (C_1+C_p)LC_c R_c^2 w^3$ $B = R_c(1-C_1 L w^2) - R_c(C_1+C_p)L w^2 + C_1 C_c R_c^2 w^2 + C_c R_c^2 w^2 (C_1+C_p)$ $C = -(C_1+C_p)(1-C_1 L w^2)(w+w^3 C_c^2 R_c^2)$ $D = -C_1(C_1+C_p)(w^2+w^4 C_c^2 R_c^2)$ $E = C$ $F = D$ $G = -(C_1+C_p)(1-C_1 L w^2)R_c w + C_1(C_1+C_p)w^3 C_c R_c^2 - C_1 w - (C_1+C_p)w - C_1 C_c^2 R_c^2 w^3 - (C_1+C_p)w^3 C_c R_c^2$ $H = -R_c C_1(C_1+C_p)w^2 + (C_1+C_p)(1-C_1 L w^2)w^2 C_c R_c^2 + (1-C_1 L w^2) - (C_1+C_p)L w^2 + (1-C_1 L w^2)w^2 C_c^2 R_c^2 - (C_1+C_p)w^4 L C_c^2 R_c^2$ Solving Equation (19) for w, the resonance frequency can be obtained which is a function of the varying capacitance $C_p$. Using the varying capacitance, the self-induced voltage can be calculated.

Figure 6A:
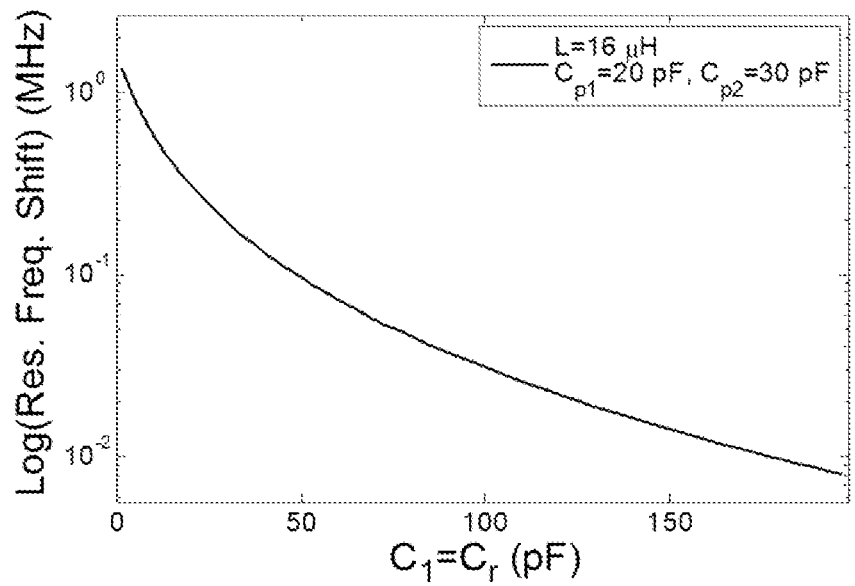
FIG. 6A illustrates effects of values of capacitance on circuit's sensitivity in detecting a shift in resonance frequency in accordance with embodiments of the present disclosure.
Figure 6B:
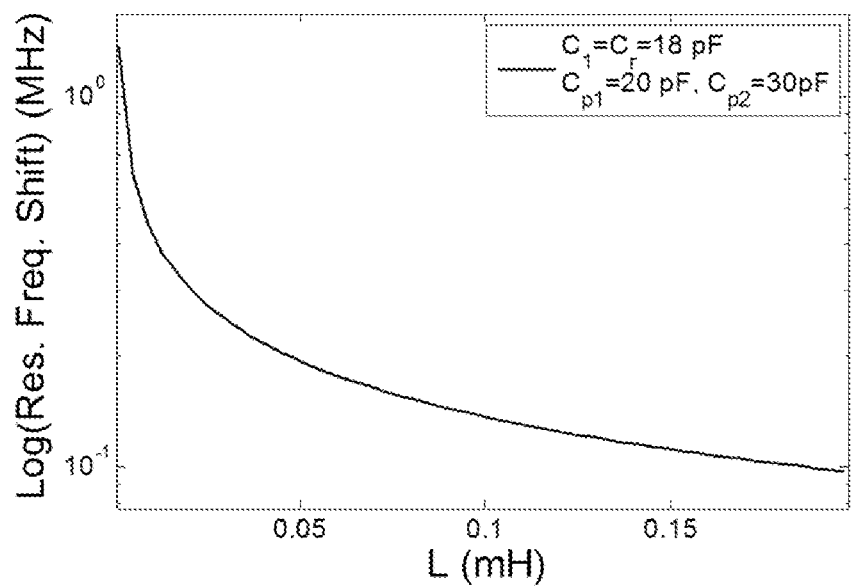
FIG. 6B illustrates effects of values of impedance on circuit's sensitivity in detecting a shift in resonance frequency in accordance with embodiments of the present disclosure.

FIGS. 6A and 6B show the effect of different values of the circuit's elements which are capacitors and inductors ($C_1$, $C_r$, and L) on the sensitivity of the circuit to measure the change in resonance frequency. Decreasing the values of $C_1$, $C_r$ and L can increase the circuit's sensitivity. FIGS. 6A and 6B illustrate the effect of $C_1$, $C_r$ and L on the circuit's sensitivity to measure shift in resonance frequency respectively. In order to optimize the circuit's response, the values of the circuit's elements can be chosen such that they fall in the sensitive region based on the results illustrated in FIGS. 6A and 6B.

Biosensor Example—Detection of Glucose in Sample Solution

The sensor system can be used for detection of glucose concentration in a sample solution in addition to other numerous sensing applications. The present disclosure provides a result of extensive experimental setup with a reference MC and a sensor MC, which is functionalized with receptor biomolecules.

A commercially available Veeco Active Probe is used as the self-sensing MC with the capability of self-excitation through the ZnO stack mounted on the base of each probe. The gold-coated surface is washed in acetone, ethanol and deionized water. A Teflon chamber was designed in order to dip the cantilever into a droplet of liquid such that the liquid only contacts the cantilever and does not proceed to the electronics attached to the probe base. A 3D stage with resolution of submicron was used in order to navigate the microcantilever in x-, y-, and z-direction and place it into the droplet.

A 0.1 M of aminoethanethiol solution was prepared by dissolving 2-aminoethanethanethiol powder into deionized water. MC was dipped into a droplet of the prepared solution for self-assembled monolayer of aminoethanethiol to form on the gold surface by attachment of thiol groups to gold.

The change in the first resonance frequency is measured and recorded.

An enzyme solution was then prepared by dissolving a definite amount of GoX into deionized water which was 5 mg/mL. 0.2% glutaraldehyde was used as a cross linking reagent being capable of binding to both the enzyme and amino groups of aminoethanethiol monolayer already formed on the gold surface. Dipping MC in enzyme solution, the aldehyde groups of glutaraldehyde react with the amino groups at one end and with GoX at other ends letting layer of enzyme grow over the surface.

Figure 5A:
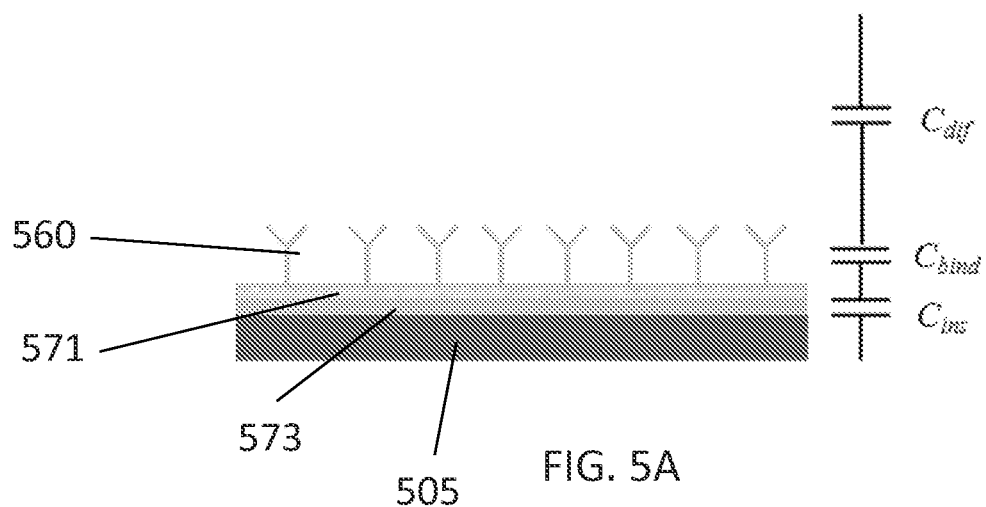
FIG. 5A illustrates a schematic view of the surface of a functionalized MC-based biosensor and FIG. 5B illustrates the molecular recognition that occurs over the surface in accordance with embodiments of the present disclosure.
Figure 5B:
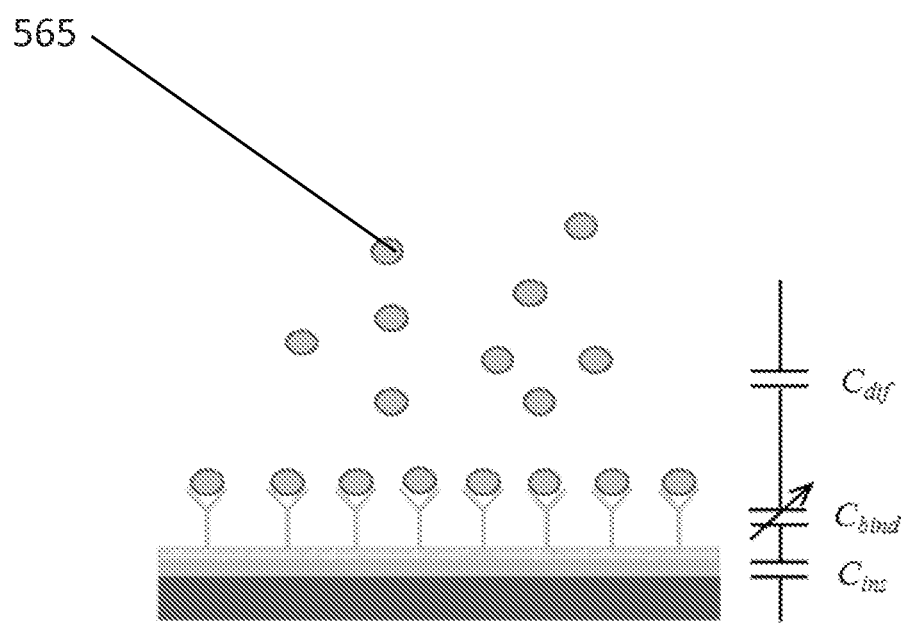

Molecular affinity that occurs over the surface of MC can result in the binding between receptor and the circuit. The model described herein presents the effect of the binding of the target biomolecule on the change of the total capacitance. Specifically, such binding between the target molecule and the coating layer on the beam surface changes the capacitance of the MC element, and thus affects the value of $C_p$ in this element (as shown by Tsouti et al., 2011, Biosensor Bioelectronic 27, pp 1-11)). The total capacitance of the MC element shown in the circuit can be modeled as three main capacitors in series including the capacitance of the insulating layer, $C_{ins}$, functionalization layer, $C_{bind}$, and diffuse layer, $C_{dif}$, as shown in FIGS. 5A-B. Therefore, total capacitance, $C_p$ can be written as $$\frac{1}{C_p} = \frac{1}{C_{ins}} + \frac{1}{C_{bind}} + \frac{1}{C_{dif}} \tag{20}$$

FIGS. 5A-B shows a microcantilever 505. On the microcantilever 505, there is an insulating layer 573, which is a coating, and a functionalization layer 571. The functionalization layer 571 immobilizes receptor biomolecules 560 that binds with target biomolecules 565. As used herein, the insulating layer can be any layer that can be employed for immobilizing molecules. As an example, gold is used as an insulating layer which is the most suitable material for immobilizing biomolecules. The material of insulating layer may vary for other purposes. As another example, polymers are employed as an insulating layer for implementing the system as a gas sensor. The insulating layer or in other words coating, can come with the commercial otherwise is should be added by the operator.

When binding occurs, the capacitance of the functionalization layer ($C_{bind}$) changes, thus the total capacitance $C_p$ changes. The change in the capacitance of MC produces a detectable shift in the resonance frequencies of the circuit which can be calculated adopting the circuit modeling presented according to some embodiments, therefore providing qualitative and quantitative insight into the amount of binding and consequently the concentration of target biomolecule in the solution.

Detection of Glucose in Air

The first resonance frequency of the MC is measured employing two different measurement systems which are i) a laser vibrometer and ii) a self-sensing circuit. A harmonic voltage was generated through oscilloscope (Agilent Infinii Vision 2000 X-Series-sw Oscilloscopes). The shift in the resonance frequency as a result of molecular binding is then measured and compared with both measurement systems.

This process of detection serves two purposes, which are: i) prove the capability of the self-sensing circuit to detect the change of frequency as a result of adsorbed mass, and ii) calibrate the mass detection in liquid by correlating the amount of adsorbed mass calculated from capacitance of the molecular interface.

The capability of the self-sensing circuit was first verified with the laser vibrometer measuring the shift in the first resonance frequency of MC as a result of GoX functionalization. The first resonance frequency of MC was measured with both a self-sensing circuit and a laser vibrometer by applying a sinusoidal voltage with a sweeping frequency of 0-100 kHz. It was measured to be 44.50 and 44.30 kHz by laser vibrometer and self-sensing circuit, respectively. The shift of 12.5 kHz was measured with both laser vibrometer and self-sensing circuit as a result of GoX-functionalization.

Figure 7A:
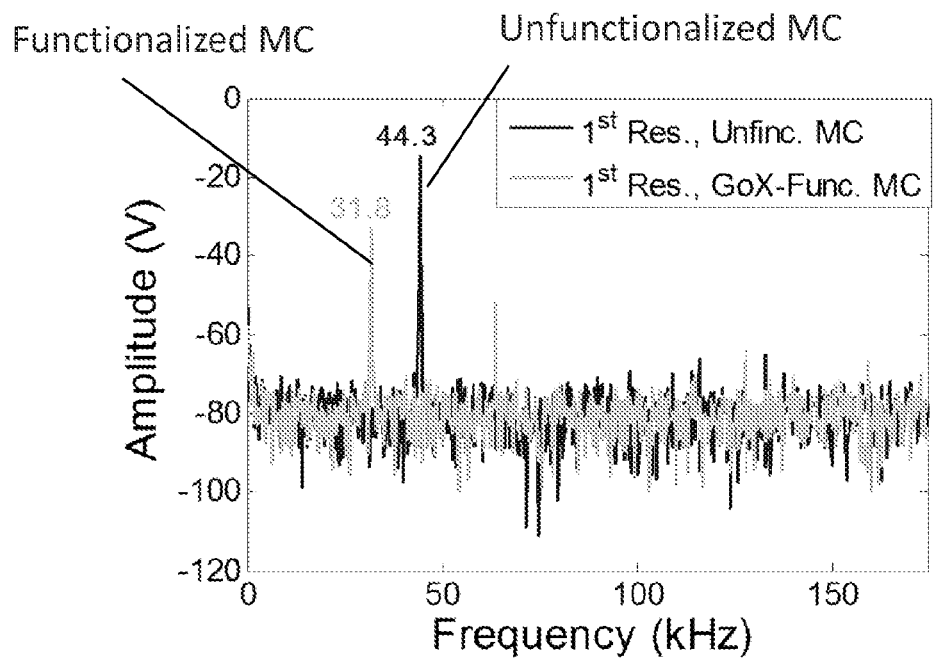
FIG. 7A illustrates a fundamental resonance frequency of the MC and shift in the resonance frequency in air as a result of GoX functionalization measured with a self-sensing circuit in accordance with embodiments of the present disclosure.
Figure 7B:
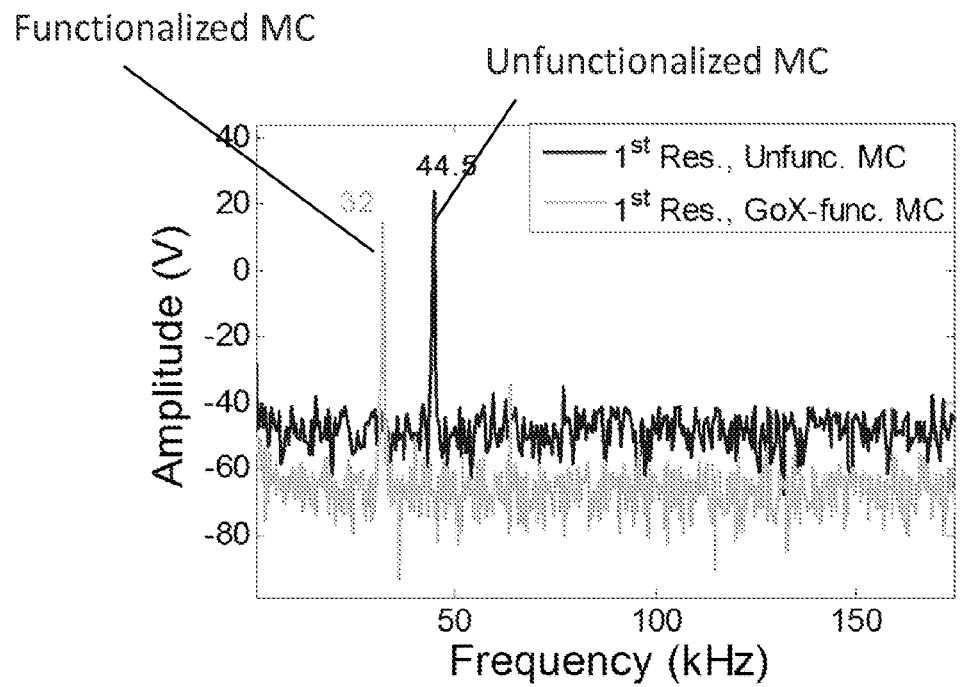
FIG. 7B illustrates a first resonance frequency of the MC and shift in the resonance frequency in air as a result of GoX functionalization measured with a laser vibrometer in accordance with embodiments of the present disclosure.
Figure 8:
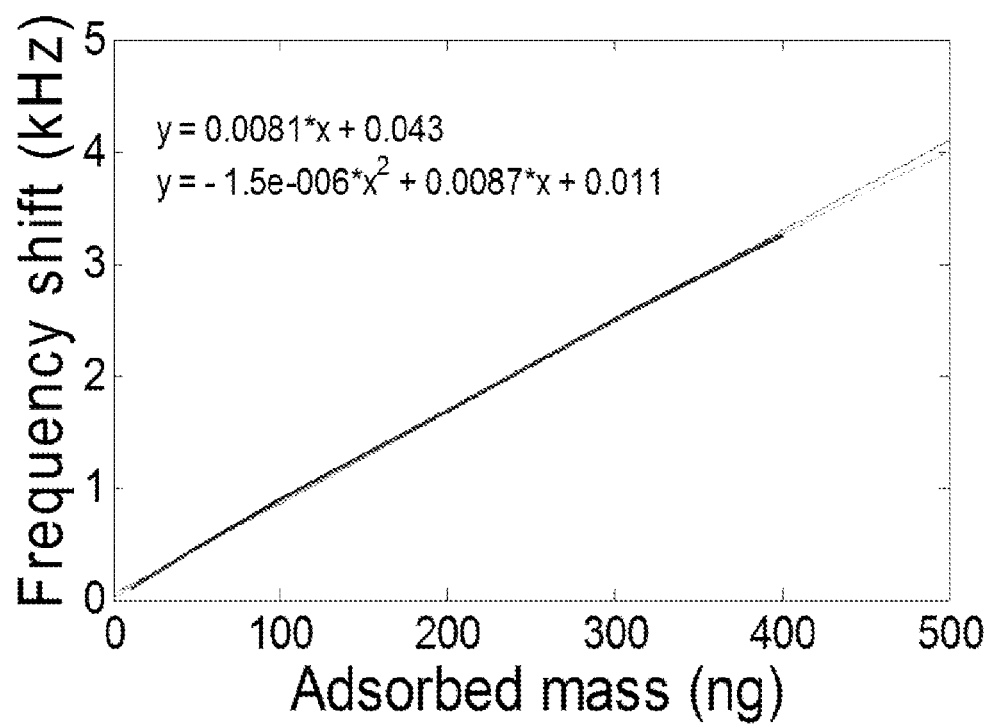
FIG. 8 illustrates quantification of amount of adsorbed mass with respect to shift in mechanical resonance frequency of the MC utilizing comprehensive distributed-parameter mathematical modeling framework in accordance with embodiments of the present disclosure.

Once the enzyme functionalization is complete, new measurement is taken by exciting the cantilever and sweeping the frequency. Taking the Fast Fourier Transform (FFT) of the response of the system provides the shift in the resonance frequency of MC as a result of formation of enzyme. FIG. 7 shows the FFT of the response of MC at its fundamental resonance. The amount of mass immobilization can be quantified having the shift in the resonance frequency of MC. Adopting the mathematical modeling and simulation illustrated in FIG. 8, the frequency shift of 12.5 kHz correlates to the mass immobilized over the surface of the amount of 1531 ng. This amount of mass detection was further correlated to a shift in a circuit's resonance frequency, which was measured in liquid media. Implementing such a comprehensive modeling framework was advantageous in calibrating the mass detection in liquid when electrical response of the system is utilized.

Detection of Glucose in Liquid

As illustrated above, in a liquid environment, molecules are detected by measuring the shift in an electrical resonance frequency of the circuit. An example of such a resonating circuit is shown in FIG. 3. The circuit, including capacitors and an inductor, resonates at a certain frequency which can be modeled calculating the equivalent impedance of the whole system.

Figure 9:
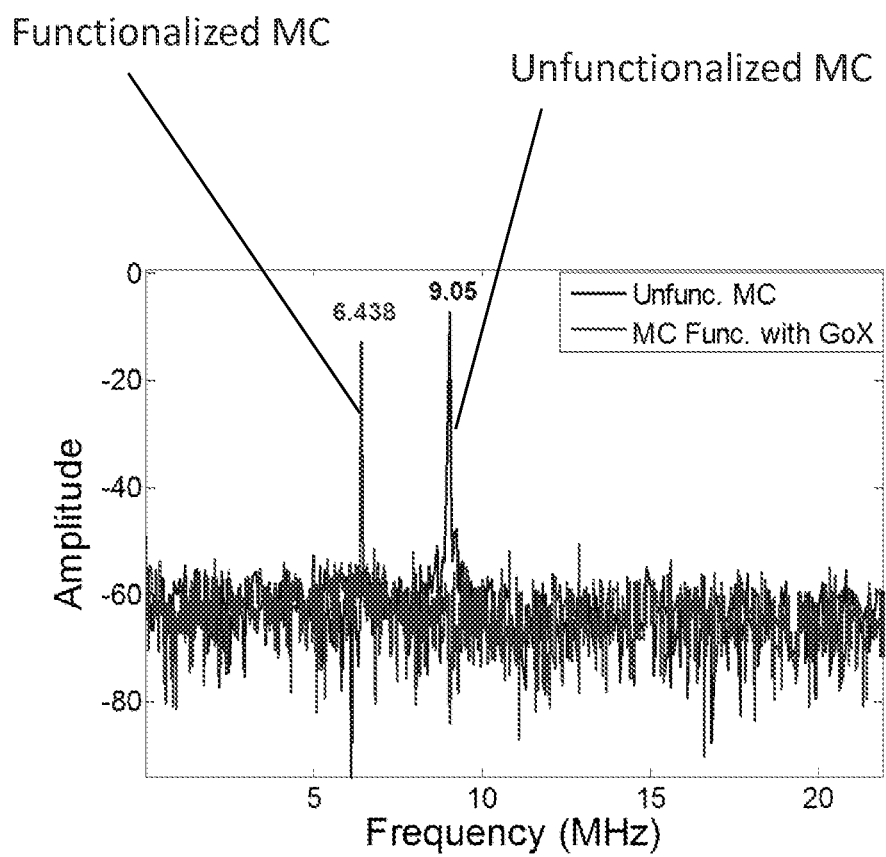
FIG. 9 illustrates a shift in the resonance frequency of the circuit as a result of GoX functionalization in accordance with embodiments of the present disclosure.
Figures 10A, 10B, 10C:
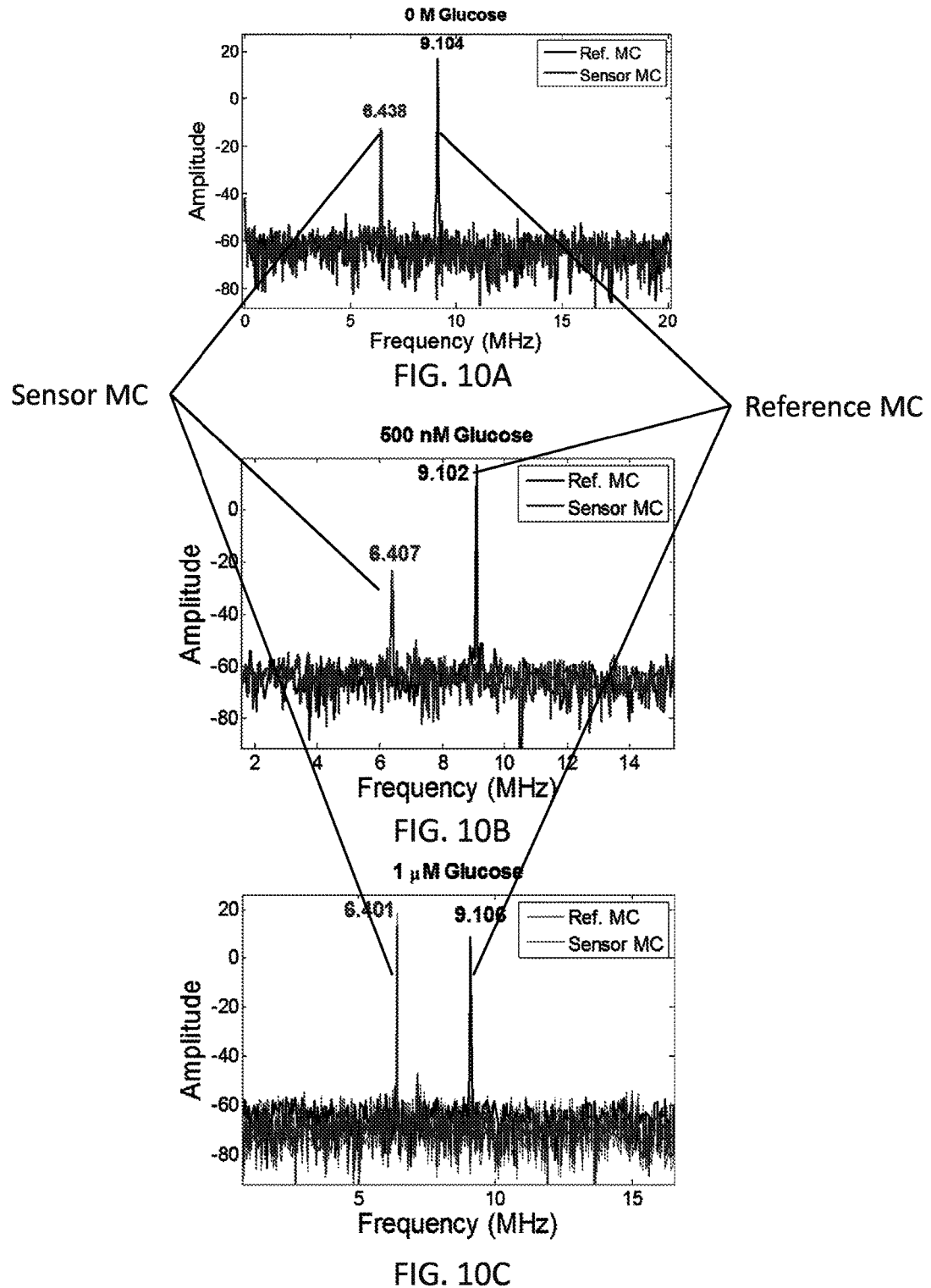
FIGS. 10A-10E illustrate resonance frequencies of the circuit consisting of sensor MC and reference MC and the shift in resonance frequency in liquid as a result of injecting a various amount of glucose in accordance with embodiments of the present disclosure.
Figures 10D, 10E:
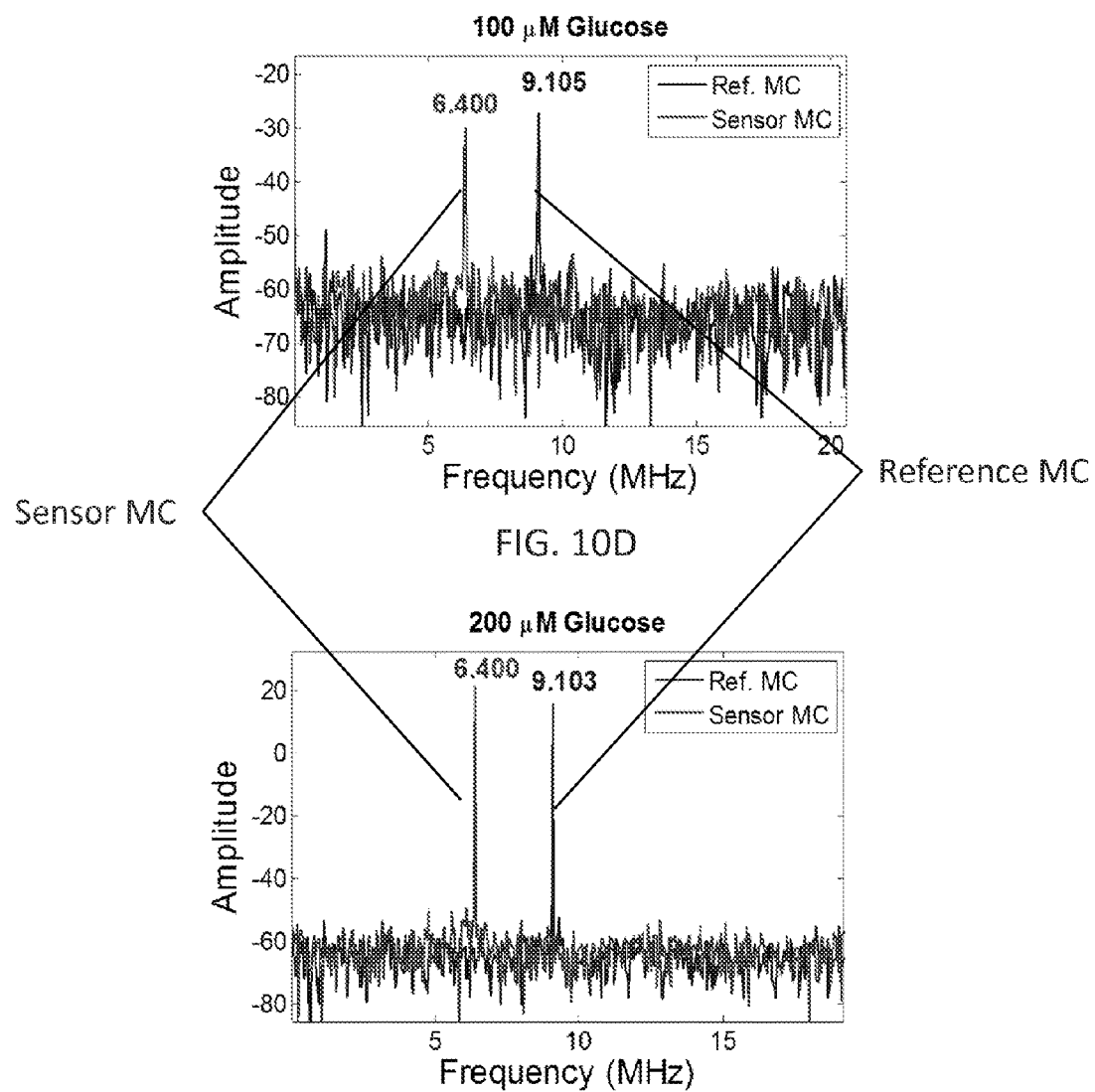

This electrical resonance frequency of the circuit was measured and recorded while putting both sensor and reference MCs in deionized water. The shift in the electrical resonance frequency as a result of GoX functionalization over the sensor MC was measured to be 2.612 MHz using the resonance frequency of the circuit as shown in FIG. 9.

Figure 11:
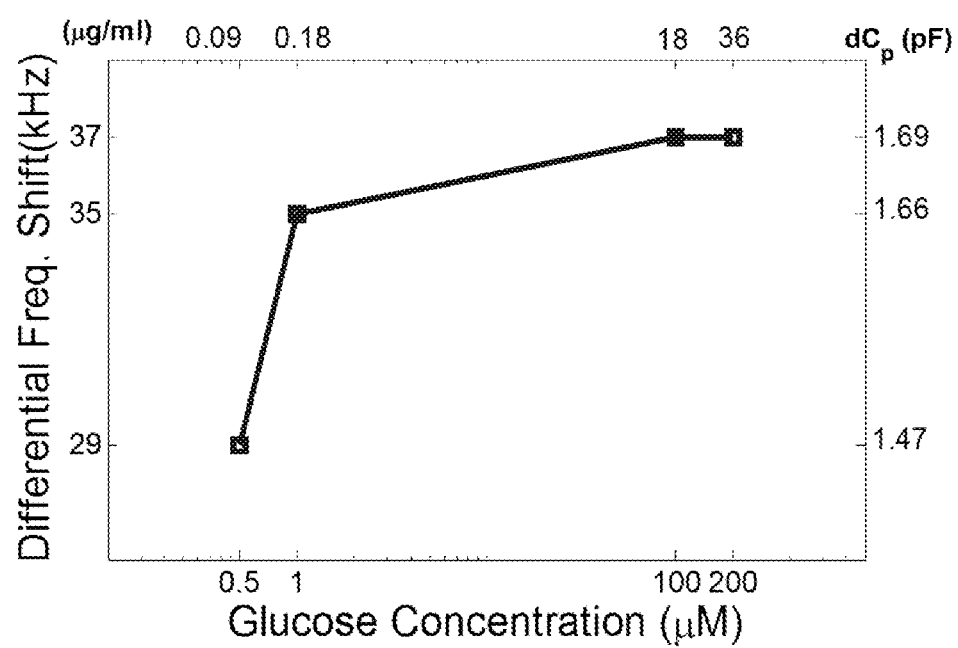
FIG. 11 illustrates a differential shift in the resonance frequency of the circuit between a sensor and a reference MC as a result of injecting different concentrations of glucose in accordance with embodiments of the present disclosure.

Different concentrations of glucose ranging from 500 nM to 200 µM was injected in deionized water and a resonance frequency of the circuit with both sensor and reference MCs was measured after each injection while exciting MCs inside the sample solution. It was shown that increasing the amount of glucose concentration in the liquid results in a higher amount of shift in the resonance frequency of the circuit with sensor MC. On the other hand the resonance frequency of the circuit with reference MC does not change significantly. FIGS. 10A-10E show the resonance frequency of the circuit for both sensor and reference MC as a result of glucose injection. It is shown that the resonance frequency of the circuit with reference MC stays within 9.102-9.106 MHz when implementing the system in solutions with different concentrations of glucose. On the other hand, detectable changes in the resonance frequency of the circuit were observed in the circuit with GoX-functionalized MC. FIG. 11 shows the differential shift ($\Delta f_{ref} - \Delta f_{sensor}$) of the circuit's resonance frequency between sensor and reference MC with respect to glucose concentration. No significant change of the resonance frequency of the circuit was observed injecting concentration of glucose higher than 200 µM indicating the saturation of functionalized surface of sensor MC.

Adopting the theoretical circuit model presented in the previous section, the corresponding change of capacitance as a result of molecular binding over the surface was calculated having the amount of shift in the circuit's resonance frequency as is depicted in FIG. 11.

Calibrating the system with the mechanical response obtained in the above section, the mount of mass adsorption was quantified and presented in table 1.

Considering the fact that the physiological level of glucose in blood is about 4-20 mM, the present platform is capable of detecting even lower amounts of glucose with very high sensitivity.

TABLE 1

Quantification of adsorbed mass with respect to circuit's resonance frequency calibrated by measured mechanical response of the system

| Circuit's resonance freq. Shift (kHz) | Amount of mass adsorption (ng) |
|---|---|
| 29 | 17.08 |
| 35 | 20.62 |
| 37 | 21.79 |

Additional description of the sensor system using piezoelectric microcantilever and resonating circuit is provided in Faegh et al., *A Cost-Effective Self-Sensing BioSensor for Detection of Biological Species at Ultralow Concentrations*, J. Appl. Phys. 113, 224905 (2013), which is incorporated herein by reference.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

What is claimed is:

1. An interchangeable sensor system comprising:
    a microcantilever comprising a beam anchored at a first end, the beam being free to vibrate on another end, wherein a piezoelectric layer is deposited on a surface of the beam;
    an input configured to receive a voltage from a voltage source for applying voltage to the piezoelectric layer; and
    a resonating circuit comprising:
        the piezoelectric layer, configured as a capacitor of the resonant circuit; and
        one or more additional electrical elements;
    wherein the voltage source is configured to apply a first AC voltage under a first condition for actuating the microcantilever at a first mechanical resonating frequency of the microcantilever and a second AC voltage under a second condition for actuating the microcantilever at a second electrical resonating frequency of the resonating circuit.

2. The sensor system of claim 1, wherein under the first condition, the first AC voltage is applied with varying frequencies encompassing the first mechanical resonating frequency of the microcantilever.

3. The sensor system of claim 1, wherein the first AC voltage is applied with varying frequencies in the range of 1-1000 kHz.

4. The sensor system of claim 1, wherein under the second condition, the second AC voltage is applied with varying frequencies encompassing the second electrical resonating frequency of the resonant circuit.

5. The sensor system of claim 1, wherein the second AC voltage is applied with varying frequencies in the range of 1-20 MHz.

6. The sensor system of claim 1, wherein the sensor system is self-sensing and the piezoelectric layer is configured to act as a self-induced voltage source.

7. The sensor system of claim 1, wherein an arrangement of the voltage source, the piezoelectric layer, and one or more additional electrical elements is configured to implement the system in self-sensing, interchangeable mode.

8. The sensor system of claim 7, wherein the self-induced voltage is measured indirectly by measuring an output voltage of the circuit.

9. The sensor system of claim 1, further comprising a detector configured to indirectly measure:
    the first mechanical resonating frequency of the microcantilever if the first AC voltage is applied under the first condition; and
    the second electrical resonating frequency of the resonant circuit if the second AC voltage is applied under the second condition.

10. The sensor system of claim 1, further comprising a coating on top of the piezoelectric layer configured to immobilize receptors for binding with molecules.

11. The sensor system of claim 1, wherein the one or more additional electrical elements comprise an inductor in parallel with the piezoelectric layer.

12. The sensor system of claim 1, wherein the one or more additional electrical elements comprise a first capacitor in series with the piezoelectric layer and a first trace between the piezoelectric layer and the first capacitor and comprising a first electrical port.

13. The sensor system of claim 12, wherein the resonating circuit further comprises:
    two electrical elements in series arranged in parallel with the piezoelectric layer, wherein a first electrical element of the two electrical elements is a second capacitor; and
    a third capacitor arranged in series with the two electrical elements and in parallel with the first capacitor, wherein a second trace between the two electrical elements and the third capacitor comprises a second electrical port.

14. The sensor system of claim 13, wherein the first electrical port and the second electrical port are configured to provide the self-induced voltage of the piezoelectric layer.

15. The sensor system of claim 1, wherein the first condition occurs when the microcantilever is in a gaseous medium, and the second condition occurs when the microcantilever is in a liquid medium.

16. The sensor system of claim 15, wherein the liquid medium is an aqueous medium.

17. The sensor system of claim 1, further comprising a detector configured to detect a medium surrounding the microcantilever.

18. The sensor system of claim 1, further comprising a detector configured to measure:
    a third mechanical resonating frequency of the microcantilever if the first AC voltage under the first condition is applied and the microcantilever are in contact with molecules; and a fourth electrical resonating frequency of the resonating circuit if the second AC voltage is applied under the second condition and the microcantilever are in contact with molecules.

19. The sensor system of claim 1, further comprising a processor configured to measure a vibrational characteristic of the microcantilever.

20. The sensor system of claim 19, wherein the vibrational characteristic comprises at least one of frequency and amplitude.

21. The sensor system of claim 1, wherein the one or more additional electrical elements comprise an inductor, capacitor, or resistor.

22. The sensor system of claim 10, wherein the molecules comprise at least one of chemical compounds, vapors, organic materials, toxins, explosives, biological species, and DNA strands.

23. The sensor system of claim 10, wherein the coating comprises gold.

24. The sensor system of claim 10, wherein the coating comprises polymers.

25. The sensor system of claim 1, further comprising a chamber covering at least part of the sensor system to expose the beam to a fluid.

26. The sensor system of claim 25, wherein the chamber comprises Teflon.

27. The sensor system of claim 25, wherein the chamber is sealed.

28. The sensor system of claim 1, further comprising an injection valve and syringe pump to operate and withdraw the fluid at a certain flow rate.

29. The sensor system of claim 1, wherein the beam comprises one or more compounds selected from the group consisting of silicon and silicon compound.

30. The sensor system of claim 29, wherein the silicon compound comprises silicon dioxide.

31. The sensor system of claim 1, wherein the piezoelectric layer comprises zinc oxide.

32. The sensor system of claim 1, wherein the piezoelectric layer comprises a piezoceramics material.

33. The sensor system of claim 32, wherein the piezoceramics material comprises one or more materials selected from the group consisting of PZT and Aluminum Nitride.

34. The sensor system of claim 1, further comprising a processor configured to measure an amount of molecules contacting the beam based on:
   the first mechanical resonating frequency if the first AC voltage is applied; and
   the second electrical resonating frequency if the second AC voltage is applied.

35. The sensor system of claim 34, wherein the step of measuring the amount of molecules comprises solving an equation of motion of the system.

36. A method of detecting molecules, the method comprising:
   providing the sensor system of claim 1 and a voltage source;
   applying, using the input to accept the voltage source, one of the first AC voltage under the first condition and the second AC voltage under the second condition to actuate the microcantilever;
   supplying molecules to the microcantilever;
   if the first AC voltage is applied, measuring i) a third mechanical resonating frequency of the microcantilever after the supply of the molecules, ii) a difference between the first and third mechanical resonating frequencies, and iii) an amount of molecules based on the difference between the first and third mechanical resonating frequencies; and
   if the second AC voltage is applied, measuring i) a fourth electrical resonating frequency of the resonating circuit after the supply of the molecules, ii) a difference between the second and fourth electrical resonating frequencies, and iii) an amount of molecules based on the difference between the second and fourth electrical resonating frequencies.

37. The method of claim 36, further comprising applying as a coating on top of the piezoelectric layer configured to bind the molecules.

38. The method of claim 36, wherein the voltage source applies the first AC voltage when the microcantilever is in a gaseous medium, and wherein the voltage source applies the second AC voltage when the microcantilever is in an aqueous medium.

39. The method of claim 38, further comprising detecting a surrounding medium of the microcantilever.

40. The method of claim 39, wherein the step of detecting the medium comprises applying a third voltage using the voltage source and determining the surrounding medium based on a movement of the microcantilever.

41. The method of claim 40, further comprising performing a Fast Fourier Transform to determine a resonance frequency of the microcantilever.

42. The method of claim 36, further comprising applying an immobilizing receptor to the coating, the immobilizing receptor designed to immobilize molecules over the coating.

43. The method of claim 42, wherein the receptor comprises an aminoethanethiol.

44. The method of claim 36, wherein the step of measuring the amount of molecules comprises solving an equation of motion of the system.

* * * * *